(12) United States Patent
Isono et al.

(10) Patent No.: US 9,101,159 B2
(45) Date of Patent: Aug. 11, 2015

(54) FERMENTATION PRODUCT CONTAINING EQUOL-PRODUCING MICROORGANISM HAVING MAINTAINED EQUOL-PRODUCING ABILITY, AND METHOD FOR PRODUCING SAME

(75) Inventors: Yoshikazu Isono, Otsu (JP); Hisako Mori, Otsu (JP); Tomomi Ueno, Osaka (JP); Rieko Endo, Osaka (JP); Megumi Kumemura, Osaka (JP); Yasuhiro Abiru, Osaka (JP); Shigeto Uchiyama, Osaka (JP)

(73) Assignee: OTSUKA PHARMACEUTICAL CO., LTD., Tokyo (JP)

(*) Notice: Subject to any disclaimer, the term of this patent is extended or adjusted under 35 U.S.C. 154(b) by 564 days.

(21) Appl. No.: 13/119,353

(22) PCT Filed: Sep. 18, 2009

(86) PCT No.: PCT/JP2009/066413
§ 371 (c)(1),
(2), (4) Date: Mar. 16, 2011

(87) PCT Pub. No.: WO2010/032838
PCT Pub. Date: Mar. 25, 2010

(65) Prior Publication Data
US 2011/0189134 A1    Aug. 4, 2011

(30) Foreign Application Priority Data
Sep. 19, 2008    (JP) .................. 2008-240937

(51) Int. Cl.
| A23L 1/20 | (2006.01) |
| A23C 9/123 | (2006.01) |
| A23C 9/13 | (2006.01) |
| A23C 11/10 | (2006.01) |
| A23L 1/03 | (2006.01) |
| A23L 1/30 | (2006.01) |

(52) U.S. Cl.
CPC ............ *A23L 1/2008* (2013.01); *A23C 9/1236* (2013.01); *A23C 9/1315* (2013.01); *A23C 11/106* (2013.01); *A23L 1/0345* (2013.01); *A23L 1/3014* (2013.01); *A23Y 2240/00* (2013.01)

(58) Field of Classification Search
None
See application file for complete search history.

(56) References Cited

U.S. PATENT DOCUMENTS

| 6,716,424 | B1 | 4/2004 | Uchiyama et al. |
| 7,345,089 | B2 | 3/2008 | Uchiyama et al. |
| 2004/0141954 | A1 | 7/2004 | Uchiyama et al. |
| 2004/0235758 | A1 | 11/2004 | Setchell et al. |
| 2006/0148045 | A1 | 7/2006 | Uchiyama |
| 2008/0131412 | A1 | 6/2008 | Uchiyama et al. |
| 2009/0311353 | A1 | 12/2009 | Kimura et al. |

FOREIGN PATENT DOCUMENTS

| CA | 2077389 | * | 9/1993 | ............. A23C 9/133 |
| EP | 1649760 | * | 4/2006 | ................ A23L 1/30 |
| JP | 2006-296434 A | | 11/2006 | |
| WO | 99/07392 A1 | | 2/1999 | |
| WO | 2005/000042 A1 | | 1/2005 | |
| WO | 2007/066655 A1 | | 6/2007 | |

OTHER PUBLICATIONS

Glenn Elert ed. "Density of Milk" http://hypertextbook.com/facts/2002/AliciaNoelleJones.shtml, 3 pages. 2002.*
Rajiv I. Dave et al., "Effectiveness of Ascorbic Acid as an Oxygen Scavenger in Improving Viability of Probiotic Bacteria in Yoghurts Made with Commercial Starter Cultures", Int. Dairy Journal, 1997, pp. 435-443, vol. 7.
Keiko Morito et al., "Interaction of Phytoestrogens with Estrogen Receptors $\alpha$ and $\beta$", Biol. Pharm. Bull, 2001, pp. 351-356, vol. 24, No. 4.
Julie Maubach et al., "Quantitation of Soy-Derived Phytoestrogens in Human Breast Tissue and Biological Fluids by High-Performance Liquid Chromatography", Journal of Chromatography B, 2003, pp. 137-144, vol. 784.
M.S. Morton, et al., "Lignans and Isoflavonoids in Plasma and Prostatic Fluid in Men: Samples From Portugal, Hong Kong, and the United Kingdom", The Prostate, 1997, pp. 122-128, vol. 32.
Tammy E. Hedlund et al., "Long-Term Dietary Habits Affect Soy Isoflavone Metabolism and Accumulation in Prostatic Fluid in Caucasian Men", American Society for Nutritional Science, Jan. 24, 2005, pp. 1400-1406, vol. 135.
Supplementary European Search Report dated Aug. 26, 2011 on European Patent Application 09814682.2, 7 pgs.

* cited by examiner

Primary Examiner — Thane Underdahl
(74) Attorney, Agent, or Firm — Sughrue Mion, PLLC (57) ABSTRACT

An object of the present invention is to provide a fermented product containing equol-producing microorganisms in the state of living cells by which equol production ability is maintained.
When producing a fermented material by using an equol-producing microorganism, with soybean powder or soybean milk as raw materials, (1) preparing a mother starter by fermentation under anaerobic conditions by using an equol-producing microorganism in the presence of a daidzein species at pH 5.0 or higher, (2) preparing a bulk starter by fermentation under anaerobic conditions by using said mother starter in the presence of a daidzein species at pH 5.0 or higher, and (3) preparing a fermented material by fermentation by using said bulk starter in a medium containing soybean powder or soybean milk, enables production of a fermented material containing microorganisms in the state of living cells in which the equol production ability is maintained.

13 Claims, 1 Drawing Sheet

FERMENTATION PRODUCT CONTAINING EQUOL-PRODUCING MICROORGANISM HAVING MAINTAINED EQUOL-PRODUCING ABILITY, AND METHOD FOR PRODUCING SAME

TECHNICAL FIELD

The present invention relates to a fermented product containing equol-producing microorganisms in the state of living cells by which the equol production ability is maintained, and a preparation process thereof. The present invention also relates to a composition containing an equol-producing microorganism in the state of a living cell, in which the equol production ability of the microorganism can be stably maintained, even after storage.

BACKGROUND ART

Isoflavones contained in soybean (for example, soybean isoflavones such as daidzein, genistein, and glycitein) have structures similar to estradiol, and an anti-estrogenic action and estrogen-like action associated with binding to an estrogen receptor (hereinafter referred to as ER). Epidemiologic studies and interventional studies on soybean isoflavones conducted thus far suggest that soybean isoflavones have a preventive effect, attributable to the anti-estrogenic action, on hormone-dependent cancers such as breast cancer and prostate cancer; and an improvement effect, attributable to the estrogen-like action, on menopausal disorders, postmenopausal osteoporosis and hyperlipidaemia.

Recently, it has been reported that the active principle of the physiological effects of these soybean isoflavones may be equol, a metabolite of daidzein. More specifically, it has been reported that equol has a greater ability to bind to ER (especially to ERβ) than soybean isoflavones, and that it has a remarkably high transition capability to target organs such as breast and prostate tissues (refer to Non-Patent Documents 1-4). Moreover, a case-control study reports that there are significantly few breast cancer and prostate cancer patients who can produce equol. The bone density- and lipid metabolism-improvement effects of soybean isoflavones were examined in postmenopausal women categorized into two groups: those who could produce equol, and those who could not. A significant improvement in those who could produce equol was observed.

Equol is produced by the metabolism of daidzein by enteric bacteria. The ability to produce equol varies between individuals, and the percentage of Japanese who can produce equol production is reportedly about 50%. That is, about 50% of Japanese are unable to produce equol (equol non-producers). Such individuals cannot enjoy the useful physiological benefits provided by the action of equol, even if they ingest soybeans and processed soybean foods. Therefore, in order for an equol non-producer to attain the useful physiological benefits provided by the action of equol, ingesting equol itself is thought to be effective.

Equol-producing microorganisms are already known; for example, *Bacteroides* E-23-15 (FERM BP-6435), *Streptococcus* E-23-17 (FERM BP-6436), *Streptococcus* A6G225 (FERM BP-6437) and *Lactococcus* 20-92 (FERM BP-10036) have been isolated from within the human intestine by the present inventors (refer to Patent Documents 1 and 2).

Consequently, it is thought that if a fermented product containing equol-producing microorganisms in the state of living cells could be provided, ingestion of an equol-producing microorganism could become possible, enabling individuals to benefit from the useful effects of the equol-producing microorganisms. However, if a fermented product is produced using an equol-producing microorganism according to common methods, the equol-production ability of the microorganism is problematically lost; and therefore, a fermented product containing equol-producing microorganisms in the state of living cells cannot be obtained. In addition, since equol-producing microorganisms have a strong tendency to lose their equol-production ability due to low pH conditions or aerobic storage, even if a fermented product could be produced while maintaining the equol-production ability of the microorganism, the equol-production ability, not being able to endure storage, would be lost at the distribution stage.

With such prior art as the background, the development of a fermented product containing microorganisms in the state of living cells by which the equol-production ability can be maintained is desired.

PRIOR DOCUMENT

Patent Document

[Patent Document 1] WO99/007392
[Patent Document 2] Wo2005/000042
[Non-patent Document 1] Morito K, Hirose T, Kinjo J, Hirakawa T, Okawa M, Nohara T, Ogawa S, Inoue S, Muramatsu M, Masamune Y. Interaction of phytoestrogens with estrogen receptors α and β. Biol Pharm Bull 24(4):351-356, 2001
[Non-patent Document 2] Maubach J, Bracke M E, Heyerick A, Depypere H T, Serreyn R F, Mareel M M, Keukeleire D D. Quantitation of soy-derived phytoestrogens in human breast tissue and biological fluids by high-performance liquid chromatography. J Chromatography B 784:137-144, 2003
[Non-patent Document 3] Morton M S, Chan P S F, Cheng C, Blacklock N, Matos-Ferreira A, Abranches-Monteiro L, Correia R, Lloyd S, Griffiths K. Lignans and isoflavonoids in plasma and prostatic fluid in men: Samples from Portugal, Hong Kong, and the United Kingdom. Prostate 32:122-128, 1997
[Non-patent Document 4] Tammy E H, Paul D M, Paul G F, Robert D, Stephen B, Kenneth J, Ray M, Lorraine G O, Kristiina W, Holly M S, Karen J G. Long-term dietary habits affect soy isoflavone metabolism and accumulation in prostatic fluid in Caucasian men. J Nutr 135: 1400-1406, 2005

SUMMARY OF INVENTION

Technical Problem

Consequently, an object of the present invention is to provide a fermented product containing an equol-producing microorganism in the state of a living cell by which the equol production ability is maintained. Another object of the present invention is to provide an equol-producing microorganism-containing composition containing an equol-producing microorganism in the state of a living cell by which the equol production ability is maintained, and which furthermore allows the equol production ability to be stably maintained even after storage.

Solution to Problem

The present inventors conducted intensive research to achieve the above objects, and found, surprisingly, that it is possible to obtain, on an industrially applicable scale, a fermented material containing equol-producing microorganisms in the state of living cells by which the equol production ability is maintained by bringing particular inventive ideas in the selection of the fermentation atmosphere, pH and the like according to the raw materials used in each step, from the preparation of a mother starter to the main fermentation using an equol-producing microorganism. The present inventors also found that by adding ascorbic acid and/or a derivative thereof to the composition containing equol-producing microorganisms in the state of living cells, the equol-production ability of the equol-producing microorganisms could be stably maintained, allowing an equol-producing microorganism-containing composition with excellent storage stability to be obtained. Specifically, the present inventors found the following.

(i) First Method for Preparing a Fermented Material

When producing a fermented material using an equol-producing microorganism with soybean powder or soybean milk as raw materials, a fermented material containing microorganisms in the state of living cells by which the equol-production ability is maintained can be prepared by: (1) performing fermentation under an anaerobic condition using an equol-producing microorganism in the presence of a daidzein species at pH 5.0 or higher to prepare a mother starter; (2) performing fermentation under an anaerobic condition using the above mother starter in the presence of a daidzein species at pH 5.0 or higher to prepare a bulk starter; and (3) performing fermentation using the above bulk starter in a medium containing soybean powder or soybean milk to prepare a fermented material.

(ii) Second Method for Preparing a Fermented Material

When preparing a fermented material using equol-producing microorganisms with milk as a raw material, a fermented material containing microorganisms in the state of living cells by which the equol-production ability is maintained can be prepared by: preparing a mother starter by conducting fermentation in the presence of a daidzein species under anaerobic conditions; and, when the milk raw material is fermented using the mother starter, conducting the fermentation in the presence of a daidzein species under a condition of pH 4.6 or higher. The fermented material can retain the equol-production ability of the equol-producing microorganism over a long period of time, and exhibits excellent storage stability. Furthermore, by performing all of the fermentation steps, i.e., from the preparation of the mother starter to the fermentation of the milk raw material, in the presence of a yeast extract, the equol-production ability of the equol-producing microorganism and the storage stability can be further improved.

(iii) Equol-Producing Microorganism-Containing Composition

A composition by which the equol-production ability of the equol-producing microorganism would not be lost even after storage can be obtained by adding ascorbic acid and/or a derivative thereof to the fermented product containing equol-producing microorganisms in the state of living cells.

The present invention has been accomplished based on these findings, and further improvements on these findings. Specifically, the present invention provides the following inventions.

Item 1. A process for producing a fermented material comprising the steps of:

(1) conducting anaerobic fermentation in a medium containing at least one type of daidzein species selected from the group consisting of daidzein glycoside, daidzein and dihydrodaidzein, by using an equol-producing microorganism, in a state where pH 5.0 or higher is maintained to prepare a mother starter;

(2) conducting fermentation by using the mother starter obtained in step (1) in the medium containing the daidzein species in a state where pH 5.0 or higher is maintained to prepare a bulk starter; and (3) conducting fermentation by using the bulk starter obtained in step (2) in a medium containing soybean powder and/or soybean milk to obtain a fermented material.

Item 2. The production process according to Item 1, wherein the equol-producing microorganism is a lactic acid bacterium.

Item 3. The production process according to Item 1, wherein the equol-producing microorganism is *Lactococcus garvieae*.

Item 4. A process for producing a fermented material comprising the steps of:

(I) conducting anaerobic fermentation in a medium containing at least one type of daidzein species selected from the group consisting of daidzein glycoside, daidzein and dihydrodaidzein by using an equol-producing microorganism to prepare a mother starter; and (II) conducting fermentation by using the mother starter obtained in step (I) in a medium containing the daidzein species compound and milk, in a state where pH 4.6 or higher is maintained to obtain a fermented material.

Item 5. The production process according to Item 4, wherein soybean hypocotyl extract is used as the daidzein species.

Item 6. The production process according to Item 4, wherein the medium used in Steps (I) and (II) further contains yeast extract.

Item 7. The production process according to Item 4, wherein the equol-producing microorganism is a lactic acid bacterium.

Item 8. The production process according to Item 4, wherein the equol-producing microorganism is *Lactococcus garvieae*.

Item 9. A fermented product containing a fermented material obtained by the production process according to any one of Items 1 to 3.

Item 10. A fermented product containing a fermented material obtained by the production process according to any one of Items 4 to 8.

Item 11. The fermented product according to Item 10, wherein the pH thereof is 4.6 or higher.

Item 12. An equol-producing microorganism-containing composition containing (A) an equol-producing microorganism in a state of a living cell, and (B) at least one member selected from the group consisting of ascorbic acid, derivatives thereof and salts thereof.

Item 13. The composition according to Item 12, wherein the (B) component is contained in a mixing proportion of 0.05 to 5 wt %.

Item 14. The composition according to Item 12, wherein the pH thereof is 5.0 or lower.

Item 15. The composition according to Item 12, which comprises a fermented material that was fermented using an equol-producing microorganism as the equol-producing microorganism in the state of a living cell.

Item 16. The composition according to Item 12, which is a fermented soybean beverage or a fermented soybean milk.

Item 17. The composition according to Item 12, wherein the equol-producing microorganism is a lactic acid bacterium.

Item 18. The composition according to Item 12, wherein the equol-producing microorganism is *Lactococcus garvieae*.

Item 19. A method for maintaining the equol production ability of an equol-producing microorganism, the method comprising: adding at least one member selected from the group consisiting of ascorbic acid, derivatives thereof, and salts thereof to a composition containing an equol-producing microorganism, in the state of a living cell.

Advantageous Effects of Invention

According to the production process of the present invention, since a fermented product containing equol-producing microorganisms in the state of living cells by which the equol production ability is maintained can be prepared, the provision of beverages and foods containing an equol-producing microorganism in the state of a living cell can be realized for the first time.

Furthermore, the production process of the present invention allows for fermentation processing while maintaining the equol production ability of the equol-producing microorganism, even when applied in an industrially applicable mass-production process. This makes the present invention highly practical commercially, and extremely useful.

When beverages and foods that contain equol-producing microorganisms in the state of a living cell by which the equol production ability is maintained are provided to humans who are unable to produce equol (equol non-producers), the equol non-producers can acquire equol production ability, and therefore benefit from the effective biological activities attributable to equol.

In addition, according to the equol-producing microorganism-containing composition of the present invention, the equol production ability of the equol-producing microorganism can be stably maintained for a long period of time; i.e., storage stability is provided, which may allow the equol-producing microorganism to sufficiently endure distribution and sales. In particular, if the equol-producing microorganism-containing composition of the present invention is in the form of a fermented soybean beverage or a fermented soybean milk, since the equol-producing microorganism in the state of a living cell is contained along with useful soybean-derived constituents such as daidzein species, it is advantageously easier for the equol-producing microorganism to generate equol in the intestine.

DESCRIPTION OF EMBODIMENTS

In the present invention, an equol-producing microorganism is a microorganism having the ability to utilize at least one type of daidzein species selected from the group consisting of daidzein glycoside, daidzein and dihydrodaidzein to produce equol (metabolic activity). Specific examples of the daidzein glycoside include daidzin, malonyldaidzin, acetyl-daidzin and the like. There are no particular limitations to the equol-producing microorganisms used in the present invention, as long as they can be ingested as food and their equol production ability can be maintained. Known microorganisms having the above-mentioned capabilities are, for example, microorganisms belonging to the genus *Lactococcus* such as *Lactococcus garvieae*; microorganisms belonging to the genus *Streptococcus* such as *Streptococcus intermedius* and *Streptococcus constellatus*; microorganisms belonging to the genus *Lactobacillus* such as *Lactobacillus mucosae*; microorganisms belonging to the genus *Bacteroides* such as *Bacteroides ovatus*; microorganisms belonging to the genus *Enterococcus* such as *Enterococcus faecium*; microorganisms belonging to the genus *Finegoldia* such as *Finegoldia magna*; microorganisms belonging to the genus *Veillonella*; microorganisms belonging to the genus *Adlercreutzia* such as *Adlercreutzia equolifaciens*; microorganisms belonging to the genus *Eubacterium* such as *Eubacterium limnosus*; microorganisms belonging to the genus *Eggerthella* such as *Eggerthella hongkongensis*; microorganisms belonging to the genus *Bifidobacterium* such as *Bifidobacterium adolescentis* and *Bifidobacterium breve*; microorganisms belonging to the genus *Slacki*; microorganisms belonging to the genus *Acinetobacter*, and the like. Among the equol-producing microorganisms, preferably lactic acid bacteria such as from the *Lactococcus* genus, the *Streptococcus* genus, the *Lactobacillus* genus and the *Bifidobacterium* genus, more preferably lactic acid bacteria belonging to the *Lactococcus* genus, and particularly preferably *Lactococcus garvieae* may be used. Equol-producing microorganisms can be isolated, for example, from inside human intestines with the presence and absence of equol production ability as an indication. Regarding the above-mentioned equol-producing microorganisms, bacteria isolated from human intestines and identified by the present inventors and others, i.e., *Lactococcus* 20-92 (FERM BP-10036), *Streptococcus* E-23-17 (FERM BP-6436), *Streptococcus* A6G225 (FERM BP-6437), and *Bacteroides* E-23-15 (FERM BP-6435) have been deposited, and these deposited bacteria can be used in the present invention. In addition, as equol-producing microorganisms, *Eubacterium limnosus* (ATCC 8486), *Eggerthella* sp. (KCC10490), *Adlercreutzia equolifaciens* (JCM14793), *Eggerthella hongkongensis* HKU10 (JCM14552), *Bifidobacterium adolescentis* TM-1 (FERM P-20325), *Bifidobacterium breve* (JCM1273), *Slackia* TM30 (FERM AP-20729), Gram-positive bacterium do03 (AHU-1763) (FERM AP-20905) and the like can also be used. Among these deposited bacteria, *Lactococcus* 20-92 is preferably used in the present invention.

Hereafter, production processes (first method and second method) for the fermented material, the fermented product, and the equol-producing microorganism-containing composition of the present invention will be detailed. The first method is a method for preparing the fermented material with soybean powder and/or soybean milk as raw materials, and the second method is a method for preparing the fermented material with milk as the raw material.

In the present specification, a mother starter is a starter (inoculum) prepared from a stock culture, and a bulk starter is a starter (inoculum) prepared from a mother starter and used in the main fermentation when preparing a large amount of fermented material.

1. Fermented Material Production Process (First Method)

The present first method for preparing a fermented material comprises a Step (1) of preparing a mother starter (hereinafter may be referred to as "mother starter-1"), a Step (2) of using mother starter-1 to prepare a bulk starter (hereinafter may be referred to as "bulk starter-1") and a Step (3) of using bulk starter-1 to prepare a fermented material with soybean powder or soybean milk as a raw material. Hereafter, the present first method for preparing the fermented material will be explained in step by step detail.

Step (1)

In the present invention, first, an equol-producing microorganism is anaerobically fermented in a medium containing a daidzein species (hereinafter may be referred to as "mother starter medium-1") in a state where pH 5.0 or higher is maintained to prepare a mother starter (hereinafter may be referred to as "mother starter-1") (Step (1)).

There is no particular limitation on the mother starter medium-1 to the extent that it allows an equol-producing microorganism to grow, and is acceptable as a food constituent; and the composition thereof is suitably set according to the types of the fermented material ultimately prepared.

Daidzein species used for mother starter medium-1 is one including one type or two or more types of daidzein species among daidzein glycoside, daidzein and dihydrodaidzein. Specific examples of daidzein glycoside include daidzin, malonyldaidzin, acetyldaidzin, and the like. In the present invention, any from a pure product of daidzein species, a crudely purified product of daidzein species and a substance containing daidzein species may be used as the daidzein species. Specific examples of substances containing daidzein species include soybean, soybean milk, soybean germ, kudzu, kudzu root, red grove, alfalfa, and extracts thereof (polar solvent extracts such as from water and hydrous alcohol), and the like. From the standpoint of stably maintaining the equol production ability of the equol-producing microorganism, the daidzein species used in the present invention is preferably soybean, soybean milk, soybean germ or extracts thereof, and particularly preferably soybean.

Here, the soybean to be used as the daidzein species is preferably soybean that has been powderized, more preferably soybean that has been steamed or boiled and powderized, and particularly preferably soybean that has been steamed or boiled at 65 to 105° C. for 30 seconds to 30 minutes, and powderized. In addition, while there is no particular limitation on the average particle diameter of the powderized soybean, from the standpoint of providing the prepared fermented material with satisfactory texture, it is generally desirable that the median diameter is on the order of approximately 50 μm or smaller. In addition, it is desirable that there are 10% or fewer particles with particle diameters of 150 μm or larger. Note that the particle diameter is measured using a laser diffraction/diffusion-type particle size distribution meter.

Examples of the mixing proportions of the daidzein species-containing substance in the mother starter medium-1 are proportions such that the total amount of the daidzein species becomes 0.002 to 0.04 wt %, preferably 0.004 to 0.02 wt %, and more preferably 0.008 to 0.012 wt %. More specifically, when soybean powder is used as the daidzein species, the proportions are such that the soybean powder converted into dry weight becomes 3 to 28 wt % in the mother starter medium-1, preferably 5 to 28 wt %, and more preferably 7 to 17 wt %. In addition, when soybean germ extract is used as the daidzein species, the proportions are such that the soybean germ extract converted into dry weight becomes 0.005 to 0.1 wt % in the mother starter medium-1, preferably 0.01 to 0.05 wt %, and more preferably 0.02 to 0.03 wt %. By including the daidzein species in such mixing proportions, an equol-producing microorganism can be grown without losing the equol production ability, allowing mother starter-1 to be obtained.

In addition, in order to promote the growth of the equol-producing microorganism, an amino acid such as arginine, vitamins such as ascorbic acid, or a trace metal such as iron pyrophosphate may be contained in mother starter medium-1. The addition of arginine in mother starter medium-1 is desirable in order for the growth of the equol-producing microorganism to become satisfactory; examples of the mixing proportions of arginine in mother starter medium-1 are 0.01 to 1 wt %, preferably 0.05 to 0.3 wt %.

Furthermore, in addition to the above constituents, nutrients such as a nitrogen source and a carbon source may be added to mother starter medium-1, as necessary.

Since mother starter medium-1 sometimes affects the flavor of the fermented material, culture media that do not negatively affect the flavor of the fermented material are given as preferable examples.

Mother starter medium-1 is prepared by mixing, emulsifying as necessary and then sterilizing given amounts of additive constituents.

In the present Step (1), anaerobic fermentation of equol-producing microorganism can be performed by conventional well-known methods that use gas packs and anaerobic jars.

In addition, in the present Step (1), anaerobic fermentation is carried out by maintaining the pH at 5.0 or greater, preferably 5.5 to 8.0 and more preferably 6.0 to 8.0. By maintaining the pH in this manner, mother starter-1, in which an equol-producing microorganism has been grown without losing the equol production ability can be prepared, allowing the equol production ability of the microorganism to be stably maintained in the fermented material ultimately obtained by the present first method of production process. The control of the pH during such anaerobic fermentation can be performed by well-known methods. For example, in the medium used, if the mixing proportion of the carbohydrate (for example, glucose or the like) utilized by the equol-producing microorganism is set to 0.5 wt % or less, preferably 0.4 wt % or less and more preferably 0.3 wt % or less, the pH does not drop even if fermentation proceeds, allowing the pH during anaerobic fermentation to be maintained in the above-mentioned ranges. In addition, the control of pH during anaerobic fermentation can also be carried out by suitably adding a pH adjuster.

The anaerobic fermentation in the present Step (1) is performed by inoculating the mother starter medium-1 with the inoculum of an equol-producing microorganism, and left to ferment anaerobically in a temperature region enabling growth of the microorganism, preferably in an optimal temperature region of the microorganism for 20 to 96 hours, more preferably 72 to 96 hours. More specifically, when using a lactic acid bacterium as an equol-producing microorganism, it is sufficient to ferment anaerobically at, for example, 35 to 39° C. for 72 to 96 hours.

The mother starter-1 obtained in this manner contains an equol-producing microorganism that has been grown and that is in a state in which the equol production ability is maintained.

The thus-obtained mother starter may be directly provided to Step (2). Alternatively, it is also possible to use the mother starter as inoculum to produce an additional mother starter, if necessary, in the same manner as described above, and then provide the additional mother starter in the subsequent production process. The production process reusing the mother starter produced in the same manner as described above can be repeated one time or more; for example, the production process can be repeated 1 to 10 times. Even if the fermentation is repeated by reusing the mother starter, as long as the above conditions can be met, equol-producing microorganisms can be contained in mother starter 1 while maintaining the equol-producing ability.

Step (2)

Next, using the mother starter-1 obtained in the previous Step (1), fermentation is carried out with a medium containing the daidzein species (hereafter may be referred to as "bulk starter medium-1") in a state where pH 5.0 or higher is maintained to prepare the bulk starter-1 (hereafter may be referred to as "bulk starter-1") (Step (2)).

There is no particular limitation on the bulk starter medium-1 to the extent that it is one containing the daidzein species, allows an equol-producing microorganism to grow, and is accepted as a food constituent; and the bulk starter medium-1 is suitably set according to the type of the fermented material.

By containing the daidzein species, bulk starter medium-1 enables growth in a state in which the equol production ability of the equol-producing microorganism is maintained. The types and mixing proportions of the daidzein species mixed into the bulk starter medium-1 are the same as in the main fermentation medium-1 described later.

In addition, the types and mixing proportions of the additive constituents mixable in addition to the daidzein species in the bulk starter medium-1 are the same as in the mother starter medium-1 described above. In addition, since bulk starter medium-1 sometimes affects the flavor of the fermented material, examples preferably include culture media that do not negatively affect the flavor of the fermented material, and more preferably include those having the same composition as the mother starter medium-1 described above.

Bulk starter medium-1 is prepared by mixing, emulsifying as necessary and then sterilizing given amounts of additive constituents.

In the present Step (2), anaerobic fermentation is carried out by maintaining the pH at 5.0 or greater, preferably 5.5 to 8.0, and more preferably 6.0 to 8.0. By maintaining the pH in this manner, bulk starter-1, in which an equol-producing microorganism has been grown without losing equol production ability, can be prepared, allowing the equol production ability of the microorganism to be stably maintained in the fermented material ultimately obtained by the present first method of production process. The control of the pH during such fermentation can be performed by methods as the same as those in the previous Step (1).

In addition, in the present Step (2), while fermentation may be carried out in either an aerobic or anaerobic atmosphere, from the standpoints of decreasing manufacturing cost, operational convenience and the like, carrying out the fermentation in an aerobic atmosphere is desirable. Although equol-producing microorganisms are prone to losing equol production ability in an aerobic atmosphere, the equol production ability can be maintained by controlling the pH condition in a specific range during the culture, even in an aerobic atmosphere.

Fermentation in the present Step (2) is performed by adding the mother starter-1 obtained in the above Step (1) to the bulk starter medium-1, for example on the order of 0.5 to 10 percent in volume, preferably on the order of 1 to 5 percent in volume, and left to ferment in a temperature region enabling the growth of the microorganism, preferably in an optimal temperature region of the microorganism for 10 to 28 hours, preferably 14 to 24 hours. More concretely, when using a lactic acid bacterium as an equol-producing microorganism, it suffices to ferment anaerobically, for example, at 35 to 39° C. for 14 to 24 hours.

The bulk starter-1 obtained in this way contains an equol-producing microorganism that has been grown and is in a state in which the equol production ability is maintained.

While the bulk starter-1 may be subjected in its current state to the following Step (3), the bulk starter-1 may, as necessary, be used as a starter (primary bulk starter), the present Step (2) performed again to prepare a secondary bulk starter, and this secondary bulk starter subjected to the following Step (3).

Step (3)

Next, using the bulk starter-1 obtained in the previous Step (2), fermentation is carried out with a medium containing a soybean powder and/or soybean milk (hereafter may be referred to as "the main fermentation medium-1") to prepare a fermented material (Step (3)).

There is no particular limitation to the main fermentation medium-1, to the extent that it contains at least one of soybean powder and soybean milk, allows an equol-producing microorganism to grow, and is acceptable as a food constituent.

A specific example of the medium containing soybean powder used as the main fermentation medium-1 is an aqueous solution containing soybean powder. From the standpoints of rendering the flavor and texture satisfactory, and furthermore suppressing the soybean odor, it is desirable to use soybean powder that has underwent heat treatment by steaming or boiling as the soybean powder used in the main fermentation medium-1. A specific example of soybean powder that has underwent heat treatment in this manner is soybean that has been steamed or boiled at 65 to 105° C. for 30 seconds to 30 minutes, and powderized. In addition, while there is no particular limitation on the average particle diameter of the soybean powder, from the standpoint of providing the prepared fermented material with a satisfactory texture, it is generally desirable that the median diameter be on the order of approximately 50 µm or smaller. In addition, it is desirable that there are 10% or fewer particles with particle diameters of 150 µm or larger. Note that the particle diameter is measured using a laser diffraction/diffusion-type particle size distribution meter. When an aqueous solution containing soybean powder is used as the main fermentation medium-1, the soybean powder is desirably added to water and subjected to a homogenizing treatment using a homogenizer or the like. By conducting a homogenizing treatment in this way, an excellent texture, in particular smoothness, can be conferred to the prepared fermented material. In addition, when an aqueous solution containing soybean powder is used as the main fermentation medium-1, while there is no particular limit on the mixing proportion of soybean powder in the aqueous solution, the soybean powder is, for example, converted into dry weight at 3 to 28 wt %, preferably 5 to 28 wt %, and more preferably 7 to 17 wt %.

When a medium containing soybean milk is used as the main fermentation medium-1, soybean milk in its current state can be used as the main fermentation medium-1. Production processes for soybean milk are well known in the corresponding technical field. Specifically, soybean milk can be prepared by grinding dehulled raw material soybean, adding the dehulled soybean to water for wet grinding to create a suspension (raw bean; bean juice), heat-treating this suspension as necessary, and then removing the solid content (okara) by solid-liquid separation treatment.

In addition, the main fermentation medium-1 may further include other additive constituents in the above composition. Since the composition of the main fermentation medium-1 influences the flavor and texture of the prepared fermented material, the other additive constituents that are to be mixed are suitably determined according to the type of fermented material that is the target of the preparation. Additive constituents mixed in the main fermentation medium-1 include, for example, sweeteners such as sucrose, sucralose and stevia; flavorants such as coffee extract and black tea extract; aroma; plant-derived constituents such as fruit juice, fruit fragments, vegetable juice and vegetable fragments; acidulants such as gluconic acid; metals such as sodium, potassium, calcium, zinc and iron; vitamins such as ascorbic acid; and the like. Since a drop in pH does not have to be suppressed in the fermentation of the present Step (3), plant-derived constituents containing sweeteners including saccharides (sucrose, glucose, and the like) and the like utilized by the equol-producing microorganism may be contained in the main fermentation medium-1.

The main fermentation medium-1 is prepared by mixing given amounts of constituents, which are emulsified as necessary and then sterilized.

For the fermentation in the present Step (3), the bulk starter-1 obtained in the above Step (2) is sufficiently added to the main fermentation medium-1 on the order, for example, of 0.5 to 10% in volume, and preferably on the order of 1 to 5% in volume; and then stirring or letting stand the mixture in a temperature region enabling the growth of the microorganism, preferably in an optimal temperature region of the microorganism for 10 to 28 hours, more preferably 14 to 24 hours. Specifically, when using a lactic acid bacterium as an equol-producing microorganism, fermenting at, for example, 35 to 39° C. for 14 to 24 hours is sufficient.

While the main fermentation in the present Step (3) may be carried out in either an aerobic or anaerobic atmosphere, from the standpoints of decreasing manufacturing cost, operational convenience and the like, performing in an aerobic atmosphere is desirable.

In addition, in the fermentation in the present Step (3), the pH during fermentation need not be particularly controlled. In general, as the fermentation in the present Step (3) proceeds, the pH in the fermented material tends to drop to on the order of 5.0 or lower.

Although a strong tendency to lose equol production ability is normally observed in an equol-producing microorganism in an aerobic atmosphere and on the order of pH 5.0 or lower, according to the present first method of production process, using the bulk starter-1 prepared through the above Steps (1) and (2) to carry out fermentation of the final stage allows a fermented material containing equol-producing microorganisms in the state of living cells by which the equol production ability is maintained to be produced.

When a medium containing soybean powder is used as the main fermentation medium-1, fermented soybean to be used as a drink or food product is ultimately obtained as a fermented material. In addition, when a medium containing soybean milk is used as the main fermentation medium-1, fermented soybean milk to be used as a drink or food product is ultimately obtained as a fermented material. The present first method of production process is suitable for preparing fermented soybean drink or food products, i.e., for the preparation of a fermented material in which a medium containing soybean powder has been fermented.

The fermented material obtained in this manner contains an equol-producing microorganism as a living cell in which the equol production ability is still maintained.

2. Fermented Material Production Process (Second Method)

The present second method for preparing a fermented material comprises Step (I) of preparing a mother starter (hereinafter may be referred to as "mother starter-2") and Step (II) of conducting fermentation using mother starter-2 with milk as raw material. Hereafter, the production process of the present invention will be described in step-by-step detail.

Step (I)

In the present invention, first, an equol-producing microorganism is anaerobically fermented in a medium containing a daidzein species (hereinafter referred to as "mother starter medium-2") to prepare a mother starter (Step (I)).

To the extent that the mother starter medium-2 allows an equol-producing microorganism to grow and is acceptable as a food constituent, there is no particular limitation on the composition thereof, which can be suitably set according to the type of fermented material.

Regarding the daidzein species used in the mother starter medium-2, while they are the same as those used in the mother starter medium-1 of the above first method, in the present second method of production process, from the standpoint of stably maintaining the equol production ability of the equol-producing microorganism, soybean hypocotyl or an extract thereof is desirable, and an extract of soybean hypocotyl is particularly desirable.

The mixing proportion of the daidzein species to be mixed into the mother starter medium-2 is the same as that of the mother starter medium-1 used in the above first method.

Also, in addition to the above constituents, the mother starter medium-2 may further contain other additive constituents. The types and mixing proportions of other additive constituent that are mixable in mother starter medium-2 are the same as those in the mother starter medium-1 used in the above first method.

In particular, the mother starter medium-2 desirably contains yeast-derived constituents such as yeast extract and yeast hydrolysate, and fermentation-promoting agents such as whey hydrolysate and casein hydrolysate. In the present second method of production process, a yeast-derived constituent, in particular yeast extract, can stably maintain the equol production ability of the equol-producing microorganism. Yeast extract may generally be added to the mother starter medium-2 at the mixing proportions of, for example, 0.0125 wt % or more, preferably 0.05 to 1 wt %, and more preferably 0.1 to 0.2 wt %. If the yeast extract concentration fulfills the above-mentioned range, the equol production ability of the equol-producing microorganism can also be stably maintained over a long period of time in the fermented material ultimately prepared.

Since mother starter medium-2 sometimes affects the flavor of the fermented material ultimately prepared, culture media include, for example, media that do not negatively affect the flavor of the fermented material; examples include media containing milk, and, as necessary, a milk fat-containing constituent, in addition to the above constituents. The types and mixing proportions of the milk and milk fat-containing constituents mixed into the mother starter medium-2 are the same as in the fermentation medium-2 described below. A desirable example of a mother starter medium-2 is one with the same composition as the main fermentation medium-2 used in Step (II).

Mother starter medium-2 is prepared by mixing, emulsifying as necessary and then sterilizing given amounts of additive constituents.

In the present Step (1), anaerobic fermentation of an equol-producing microorganism can be performed by conventionally known methods using gas packs and anaerobic jars.

In addition, in the present Step (I) it is desirable to maintain the pH during anaerobic fermentation at 4.6 or higher, preferably 5.0 to 7.0, and more preferably 5.5 to 6.5. By maintaining the pH in this manner, the effects of the present invention of growing an equol-producing microorganism without losing equol production ability, and also stably maintaining the equol production ability of the microorganism after preparation can be enhanced. The control of the pH during such anaerobic fermentation can be performed by methods as the same as those in Step (1) in the above first method.

The anaerobic fermentation in the present Step (I) is performed by inoculating the mother starter medium-2 with the inoculum of an equol-producing microorganism, and leaving the mixture to ferment anaerobically in a temperature region enabling growth of the microorganism, preferably in an optimal temperature region of the microorganism for 20 to 28 hours, more preferably 22 to 26 hours. Specifically, when using a lactic acid bacterium as an equol-producing microorganism, fermenting anaerobically at, for example, 35 to 39° C. for 22 to 26 hours is sufficient.

The mother starter-2 obtained in this manner contains an equol-producing microorganism that has been grown and that is in a state in which the equol production ability is maintained.

Step (II)

Next, using the mother starter-2 obtained in the previous Step (I), a medium containing the daidzein species (hereafter referred to as "the main fermentation medium-2") is fermented in a state where pH 4.6 or higher is maintained (hereafter may be referred to as "the main fermentation") (Step (II)).

In the present Step (II), while the mother starter-2 obtained in the above Step (I) may be added to the main fermentation medium-2 to carry out the main fermentation, when preparing a large amount of fermented milk product, the mother starter-2 may be used to further prepare a bulk starter (hereafter may be referred to as "bulk starter-2"), and the bulk starter-2 added to the main fermentation medium to perform the main fermentation.

For the medium used in the preparation of the bulk starter-2 (hereafter noted "bulk starter medium-2"), a medium containing the daidzein species is used. By mixing the daidzein species in this manner, growth is possible in a state that maintains the equol production ability of the equol-producing microorganism. The types and mixing proportions of the daidzein species to be mixed into the bulk starter medium-2 are the same as those in the above mother starter medium-2.

There is no particular limitation on the bulk starter medium-2, to the extent that it contains the daidzein species, allows an equol-producing microorganism to grow, and is acceptable as a food constituent; and the bulk starter medium-2 is suitably set according to the type of the fermented material. The types and mixing proportions of the additive constituents mixable in addition to the daidzein species in the bulk starter medium-2 are the same as those in the mother starter medium-2 described above. Note that, in order to stably maintain the equol production ability of the equol-producing microorganism, it is desirable that the bulk starter medium-2 also contains a yeast-derived constituent, in particular a yeast extract. In addition, since the bulk starter medium-2 sometimes affects the flavor of the fermented material, the bulk starter medium-2 desirably contains milk, and, as necessary, a milk fat-containing constituent.

Examples of the bulk starter medium-2 preferably include a medium that does not negatively influence the flavor of the fermented material, and, more preferably, is one with the same composition as the main fermentation medium-2.

The bulk starter medium-2 is prepared by mixing, emulsifying as necessary, and then sterilizing given amounts of mixing constituents.

In order to prepare the bulk starter-2, the mother starter-2 obtained in the above Step (I) is added to the bulk starter medium-2 on the order, for example, of 1 to 10% in volume, preferably on the order of 1 to 5% in volume; and left to ferment in a temperature region enabling the growth of the microorganism, preferably in an optimal temperature region of the microorganism for 20 to 28 hours, more preferably 22 to 26 hours. Specifically, when using a lactic acid bacterium as an equol-producing microorganism, fermenting at, for example, 35 to 39° C. for 22 to 26 hours is sufficient.

In the preparation of the bulk starter-2, while fermentation may be carried out in either an aerobic or anaerobic atmosphere, from the standpoint of decreasing the manufacturing cost, operational convenience and the like, performing in an aerobic atmosphere is desirable.

In addition, in the preparation of the bulk starter-2, while there is no particular limitation regarding the pH during fermentation, maintaining a pH of 4.6 or higher, preferably 5.0 to 7.0, and more preferably 5.5 to 6.5 is desirable. By maintaining the pH in this manner, the equol-producing microorganism can be grown without losing the equol production ability. Such control of pH during fermentation can be carried out by methods as the same as those in the previous Step (I).

While the bulk starter-2 may be subjected in its current state to the following main fermentation, the bulk starter-2 may, as necessary, be used as a starter (primary bulk starter), with fermentation carried out again in the same conditions as those for the bulk starter-2 to prepare a secondary bulk starter, and then the secondary bulk starter subjected to the following main fermentation.

There is no particular limitation regarding the main fermentation medium-2 used in the present Step (II), to the extent that the main fermentation medium-2 contains the daidzein species and milk, allows an equol-producing microorganism to grow, and is acceptable as a food constituent.

The daidzein species used in the main fermentation medium-2 are the same as those used in the mother starter medium-1 of the above first method. However, from the standpoint of stably maintaining the equol production ability of the equol-producing microorganism, in the present second method of production process, soybean hypocotyl or extract thereof is desirable, and extract from soybean hypocotyl is particularly desirable.

The mixing proportions of the daidzein species to be mixed into the main fermentation medium-2 are the same as those in the above mother starter medium-2.

In addition, as the milk used in the main fermentation medium-2, a milk acceptable as food is sufficient. Examples of such milk include animal milks such as cow milk, goat milk and sheep milk; nonfat milk; reconstituted milk obtained by dissolving non-fat dry milk or dry whole milk; and the like.

In addition, in the main fermentation medium-2, in order to improve the flavor of the prepared fermented material, the main fermentation medium-2 may contain milk fat-containing constituents such as fresh cream and butter. General examples of the mixing proportions of these milk fat-containing constituents converted into the amount of milk fat are 0.1 to 4.5 wt %, preferably 0.5 to 4.2 wt %, and more preferably 1.0 to 3.5 wt %.

In addition, the types and mixing proportions of the additive constituents that are mixable in the main fermentation medium-2 in addition to the above constituents are the same as those in the above mother starter medium-2. Note that, in order to stably maintain the equol production ability of the equol-producing microorganism, it is desirable that the main fermentation medium-2 also contains a yeast-derived constituent, in particular yeast extract.

The main fermentation medium-2 is prepared by mixing, emulsifying as necessary and then respectively sterilizing a given amount of milk, the daidzein species, and, as necessary, other additives constituents.

For the main fermentation in the present Step (II), it is sufficient to add the mother starter-2 obtained in the above Step (I) or the above bulk starter-2 to the main fermentation medium-2 on the order, for example, of 1 to 10% in volume, preferably 1 to 5% in volume; and stirring or letting stand the mixture in a temperature region enabling the growth of the microorganism, preferably in an optimal temperature region of the microorganism for 20 to 28 hours, more preferably 22 to 26 hours. Specifically, when using a lactic acid bacterium as an equol-producing microorganism, fermenting at, for example, 35 to 39° C. for 22 to 26 hours is sufficient.

While the main fermentation in the present Step (II) may be carried out in either an aerobic or anaerobic atmosphere, from the standpoints of decreasing the manufacturing cost, operational convenience and the like, performing in an aerobic atmosphere is desirable.

In addition, in the main fermentation in the present Step (II), the pH during fermentation is maintained at 4.6 or higher, preferably 5.0 to 7.0, and more preferably 5.5 to 6.5. By maintaining the pH in this manner, an equol-producing microorganism can be grown without losing the equol production ability, and the equol production ability of the microorganism can be stably maintained even after preparation. The control of the pH during such anaerobic fermentation can be performed by methods as the same as those in Step (I).

In the present second method of production process, fermented milk is prepared as the fermented material. The fermented material contains an equol-producing microorganism in the state of a living cell without losing the equol production ability.

3. Fermented Product

Furthermore, the present invention provides a fermented product containing the fermented material obtained in the above first method and second method. That is to say, the fermented materials obtained in the above first method and second method may be provided as fermented products in their current state; or, as necessary, by mixing additive constituents such as, for example, sweeteners such as sucrose, sucralose and stevia; flavorants such as coffee extract and black tea extract; aroma; plant-derived constituents such as soybean powder, soybean fragments, fruit juice, fruit fragments, vegetable juice and vegetable fragments; metals such as sodium, potassium, calcium, zinc and iron; vitamins such as ascorbic acid; gelation agents; stabilizers such as gluconic acid; and diluents such as water. Above all, the fermented material obtained by the above described first method is provided desirably as a fermented product mixed with an aqueous solution containing soybean powder.

In the present fermented product, there is no particular limit regarding the mixing proportions of the fermented materials obtained in the above first method and second method; for example, the mixing proportions may be 5 to 100 wt %, preferably 10 to 100 wt %.

There is no particular limitation regarding the pH of the present fermented product. For example, if the focus is on stably maintaining the equol production ability of the equol-producing microorganism inside the fermented product for a long period of time, it is desirable that the pH be adjusted to 4.6 or higher, preferably 5.0 to 7.0, and more preferably 5.5 to 6.5. On the other hand, with proliferation of contaminating bacteria in the neutral region being a concern, if the focus is on suppressing the proliferation of contaminating bacteria, it is desirable that the pH be adjusted to 5.0 or lower, preferably 4.0 to 4.8, and more preferably 4.2 to 4.6.

The morphology of the present fermented product is determined by the type of the main fermentation medium used at the time of preparation, the type of the fermented material obtained in the above first method or second method, the type of additive constituent mixed in the fermented material, and the like; and may be any of a liquid form, semi-solid form, solid form or gel form. Desirable examples of the morphology of the present fermented product include fermented soybean drinks and foods, fermented soybean milk drinks and foods, and fermented milk and the like. Here, fermented milk includes yogurt (hard type, soft type, drink type), lactic acid bacterium beverages, and the like.

Since the present fermented product contains an equol-producing microorganism in the state of a living cell, distribution and sales under low temperature is desirable.

Since the present fermented product contains an equol-producing microorganism that maintains the equol production ability even in the state of a living cell, various biological activities and pharmacological activities based on the microorganism can be expressed. Consequently, the present fermented product can be specifically used in health drinks and foods, dietary supplement drinks and foods, functional drinks and foods, drinks and foods for the sick, and the like, in addition to general drinks and foods.

For example, since the present fermented product, when consumed, allows equol to be generated by the action of the equol-producing microorganism in the intestines, and allows the biological activities of equol to be received effectively, the present fermented product is useful in applications such as, for example: the prevention or treatment of diseases and symptoms such as menopausal disorders, osteoporosis, prostate hypertrophy and metabolic syndrome; decreasing blood cholesterol value; skin whitening; improvement of acne; intestinal regulation; improvement of obesity; and diuresis. Among these, the present fermented product is particularly useful in the prevention or improvement of indefinite complaint, or in symptoms associated with menopause (for example, osteoporosis, menopausal disorders and the like) in middle-age and older females.

While the daily intake of the present fermented milk product varies according to the cell count of the equol-producing microorganism in the present fermented milk product, the age and body weight of the consumer, the number of ingestions and the like, the daily adult intake can be, for example, a quantity corresponding to 10 to 500 g of the present fermented product.

4. Equol-Producing Microorganism-Containing Composition

By adding at least one member selected from the group consisiting of ascorbic acid, derivatives thereof and salts thereof to the composition containing an equol-producing microorganism in the state of a living cell, the equol production ability of the equol-producing microorganism can be stably maintained even under low pH or aerobic storage conditions; and the loss of the equol production ability of the equol-producing microorganism in the composition can be suppressed, even if stored for a long period of time. Thus, the present invention further provides an equol-producing microorganism-containing composition (hereafter may be referred to simply as "the present composition") containing an equol-producing microorganism in the state of a living cell (hereafter may be referred to as simply "(A) constituent"), as well as at least one member selected from the group consisiitng of ascorbic acid, derivatives thereof and salts thereof (hereafter may be referred to simply as "(B) constituent").

In the present composition, isolated or crudely purified living cells of an equol-producing microorganism may be used as the equol-producing microorganism; in addition, a fermented material fermented using an equol-producing microorganism may also be used.

While there is no particular limitation regarding the concentration of equol-producing microorganism contained in the present composition, examples of the concentration include $1\times10^5$ to $10^{10}$ cfu/g, preferably $1\times10^6$ to $10^{10}$ cfu/g, and more preferably $1\times10^7$ to $10^{10}$ cfu/g.

In the present composition, (B) constituent is mixed in order to stably maintain the equol production ability of the equol-producing microorganism. Among the (B) constituents, there is no particular limitation regarding the derivatives of ascorbic acid, as long as they have a substituent bonded to ascorbic acid via an ester bond or an ether bond, and are allowed as food constituents; specific examples include ascorbyl 2,6-dipalmitate, ascorbyl 6-stearate, ascorbyl 2-phosphate, ascorbyl 2-sulfate, ascorbyl 2-glucoside, ascorbyl glucosamine, ascorbyl 6-palmiate, L-ascorbyl tetra-isopalmitate, ascorbyl tetra 2-hexyl decanoate, and the like. In addition, examples of salts of ascorbic acid and derivatives thereof, although not particularly limited as long as they are acceptable as food constituents, include alkaline metal salts such as alkaline metal salts of sodium. Desirable examples among the (B) constituents include ascorbic acid and salts thereof. In the present composition, the (B) constituents may be used singly or in combination.

General examples of the mixing proportions of the above (B) constituent in the present composition include 0.05 to 5 wt %, preferably 0.05 to 2 wt %, and more preferably 0.1 to 2.0 wt %. By fulfilling such mixing proportions, the equol production ability of the equol-producing microorganism can be stably retained.

There is also no particular limitation regarding the pH of the present composition, which is suitably set according to the type of the present composition. From the standpoint of suppressing the proliferation of contaminating bacteria in the present composition, it is desirable that the pH be adjusted to 5.0 or lower, preferably 4.0 to 4.8, and more preferably 4.2 to 4.6. Although the tendency of an equol-producing microorganism to lose the equol production ability generally becomes stronger under an environment of pH 5.0 or lower, after which the equol production ability can no longer be stably maintained, according to the present composition, the equol production ability of the equol-producing microorganism can be stably maintained even under conditions in which the pH is 5.0 or lower, due to the action of ascorbic acid and/or derivative thereof.

The present composition may contain, as necessary, additive constituents such as, for example, sweeteners such as sucrose, sucralose and stevia; flavorants such as coffee extract and black tea extract; aroma; plant-derived constituents such as fruit juice, fruit fragments, vegetable juice and vegetable fragments; metals such as sodium, potassium, calcium, zinc and iron; vitamins such as β-carotene; gelation agents; stabilizers such as gluconic acid; and diluents such as water. Here, the additive constituents to be mixed in the present composition are preferably ones that are not utilized by the equol-producing microorganism so as not to lose storage stability.

There is also no particular limitation regarding the morphology of the present composition, which may be any of a liquid form, semi-solid form, solid form or gel form.

One example of a desirable morphology of the present composition is a fermented product obtained by adding ascorbic acid and/or a derivative thereof, and, if necessary, other additive constituents to a fermented material that was fermented using an equol-producing microorganism. Here, examples of the fermented material fermented using an equol-producing microorganism preferably include fermented materials prepared by the above first method and second method. In addition, specific examples of the fermented product include fermented soybean drinks and foods, fermented soybean milk drinks and foods, fermented milk, and the like. Here, fermented milk includes yogurt (hard type, soft type, drink type), lactic acid bacterium beverage, and the like. Among these the fermented products are preferably fermented soybean drink and food, and fermented soybean milk drink and food; and more preferably fermented soybean drink and food.

In addition, another preferred example of the morphology of the present composition is a composition containing isolated or crudely purified living cells of equol-producing microorganism, ascorbic acid and/or a derivative thereof, edible carriers, as well other additive constituents, as necessary. Examples of edible carriers include an aqueous solution containing soybean powder, soybean milk, water, edible gel, milk, various salt solutions and the like.

Since the present fermented product contains an equol-producing microorganism in the state of a living cell, distribution and sales under low temperature is desirable.

Since the present composition contains an equol-producing microorganism in a state that maintains the equol production ability even as a living cell, various biological activities and pharmacological activities based on the microorganism can be expressed. Consequently, the present composition can be used in the fields of medicine, or drink and food.

When the present composition is used in the field of drink and food, the present composition is provided, as specific health drinks and foods, dietary supplement drinks and foods, functional drinks and foods, drinks and foods for the sick, and the like, in addition to general drinks and foods.

For example, because the present composition, when consumed, allows equol to be generated by the action of the equol-producing microorganism in the intestines, and allows individuals to benefit effectively from the biological activities and pharmacological activities of equol, the present composition is preferably used by people seeking benefit from the action of equol in the fields of medicine, or drink and food. Specifically, the present composition is useful in applications such as, for example, prevention or treatment of diseases and symptoms such as of menopausal disorders, osteoporosis, prostate hypertrophy and metabolic syndrome; decreasing blood cholesterol value; skin whitening; improvement of acne; intestinal regulation; improvement of obesity; and diuresis. Among these, the present composition is particularly useful in the prevention or improvement of indefinite complaint, or symptoms associated with menopause (for example, osteoporosis, menopausal disorders and the like) in middle-age and older females.

While the daily intake of the present composition varies depending on the cell count of the equol-producing microorganism in the present fermented milk product, the age and body weight of the consumer, the number of ingestions and the like, one example of a daily adult intake is a quantity corresponding to 10 to 500 g of the present composition.

In addition, as described above, by adding the above (B) to the composition containing an equol-producing microorganism in the state of a living cell, the equol production ability of the equol-producing microorganism can be stably retained, and the loss of the equol production ability of the equol-producing microorganism can be suppressed, even if stored for a long period of time. Consequently, the present invention further provides a method for maintaining the equol production ability of the equol-producing microorganism comprising adding at least one member selected from the group consisiting of ascorbic acid, derivatives thereof, and salts thereof to the composition containing an equol-producing microorganism in the state of a living cell. The equol production ability is measured according to the method described in the following examples. As specific embodiments of the storage stabilization method, the contents of the description of the above equol-producing microorganism-containing composition are adopted.

EXAMPLES

Hereafter, the present invention will be described in detail based on examples; however, the present invention is not limited to these examples.

The soybean powder used in the following examples and comparative examples was prepared by the following method.

Preparation of Soybean Powder Solution

Dehulled soybeans were peeled, divided into halves, and subjected to steam treatment. The steam treatment continued to send steam against the dehulled soybeans until a temperature of 100° C. was reached, after which the temperature was maintained at 100° C. for 140 seconds. Next, the soybeans after steam treatment were converted into flakes after being passed between the rollers of a roller mill. Thereafter, the soybeans in flake form were dried by performing hot air drying at 80° C. until the moisture content became on the order of 3 to 6%; and the flakes were then ground with an air grinder to obtain a soybean powder. Grinding with the air grinder was performed so that the number of ground particles with a diameter of 150 μm or larger became 10% or less.

A predetermined amount of soybean powder obtained as described above was then added to suitable amounts of sodium hydrogen carbonate and trisodium citrate dissolved in water, dispersed and dissolved, and left to swell for 15 minutes or longer. Next, the obtained solution was heated at 95° C. for 10 minutes to extract water-soluble constituents in the soybean powder, as well as to inactivate enzymes such as LOX and trypsin inhibitor contained in the soybean powder. After heating, while a temperature of 80° C. or higher was maintained, a suitable amount of citric acid was added to reverse the pH to neutral. Thereafter, homogenization treatment was carried out using a homogenizer (LAB40 manufactured by GAULIN), under conditions in the range of 200-1,000 kgf/cm$^2$ to prepare a soybean powder solution (containing 14 wt % of soybean powder by dry weight).

Example 1

Preparation of Fermented Soybean Food by the First Method, and Evaluation of the Fermented Soybean Food 1. Preparation of Fermented Soybean Food

*Lactococcus garvieae* (*Lactococcus* 20-92 strain, FERM BP-10036) having equol production ability, was used to carry out the preparation of the mother starter, the preparation of the bulk starter, the main fermentation, and container filling, under the following conditions.

Preparation of Mother Starter

A mother starter medium was prepared by autoclave sterilization (121° C., 15 minutes) of 100 ml of a solution (pH 7.48) containing 80 wt % of soybean powder solution (containing 14% soybean powder in dry weight), 0.1 wt % of glucose, 0.1 wt % of L-arginine, and the remainder in purified water. This starter medium was inoculated with an inoculum of *Lactococcus* 20-92 strain, and an anaerobic culture was carried out with a gas pack at 37° C. for 96 hours to obtain a mother starter (pH 6.64).

Preparation of Bulk Starter

A bulk starter medium was prepared by autoclave sterilization (121° C., 15 minutes) of 5 L of a solution (pH 7.48) containing 80 wt % of soybean powder solution (containing 14% soybean powder by dry weight), 0.1 wt % of glucose, 0.1 wt % of L-arginine, and the remainder in purified water. This starter medium was inoculated with the mother starter obtained above to a 1% volume, and a stationary culture was carried out at 37° C. for 15 hours under aerobic conditions to obtain a bulk starter (pH 6.72).

Main Fermentation

The main fermentation medium was prepared by sterilizing 200 L of a solution (pH 6.78) containing 50 wt % of soybean powder solution (containing 14% soybean powder in dry weight), 6 wt % of carrot juice (Miyazaki Nokyokaju), 6 wt % of pumpkin paste (Nagano Sanyo Foods), and the remainder in purified water with a double-tube sterilizer at 95° C. for 30 seconds. The main fermentation medium recovered after sterilization was inoculated with 4 L of the bulk starter obtained above, and a stationary culture was carried out at 37° C. for 15 hours under aerobic conditions to obtain a fermented soybean solution (pH 4.56).

Mixing of Secondary Raw Materials and Container Filling

A secondary raw material solution was obtained by sterilizing 800 L of a solution containing 65 wt % of soybean powder solution (containing 14% soybean powder by dry weight), 7.4 wt % of sugar, 1.0 wt % of gelation agent formulation FG2524 (manufactured by Nitta Gelatin), 0.8 wt % of gluconic acid, 0.4 wt % of aroma, 0.1 wt % of L-ascorbic acid and the remainder in purified water with a double-tube sterilizer at 95° C. for 30 seconds. 80 parts by weight of the secondary raw material solution and 20 parts by weight of the fermented soybean solution obtained above were mixed at 37 to 40° C. While maintaining the temperature of the mixed solution, a polyethylene cup (130 ml total capacity, 71 mm mouth diameter) was filled with 100 g of solution in a sterile manner, and sealed with an aluminum lid. The material was placed inside a refrigerator at 5° C. and solidified by cooling to obtain a fermented soybean food containing *Lactococcus garvieae* 20-92 strain living cells.

2. Various Evaluations

The sealed fermented soybean food obtained above was stored at 10° C. for 3 weeks. The pH of the fermented soybean food was measured immediately after preparation, 1 week after preparation, weeks after preparation, and 3 weeks after preparation; furthermore, the cell count of *Lactococcus garvieae* contained in the fermented soybean food, and the presence or absence of the equol production ability of *Lactococcus garvieae* contained in the fermented soybean food were evaluated by the following methods. In addition, the cell count of *Lactococcus garvieae* and the equol production ability of *Lactococcus garvieae* of each of the mother starter and the bulk starter prepared above and the fermented product after the main fermentation were measured in same fashion.

Measurement of Cell Count of *Lactococcus garvieae*

The measurement of viable cell count of *Lactococcus garvieae*, was determined by performing a pour culture using BCP-added plate count agar medium (manufactured by Nissui Pharmaceutical Co., Ltd.) at 37° C. for 72 hours, and measuring the number of colonies grown.

Measurement of Presence or Absence of Equol Production Ability of *Lactococcus garvieae*

200 μl of fermented soybean food was added to 5 ml of modified GAM bouillon containing daidzein at a concentration of 10 μg/ml (manufactured by Nissui Pharmaceutical Co., Ltd.) to carry out an anaerobic culture at 37° C. for 96 hours with a gas pack. Then, the obtained culture solution was subjected to HPLC analysis to determine the equol amount in the culture solution. HPLC analysis was performed as follows. First, 0.5 ml of the culture solution was added to 5.0 ml of ethyl acetate to perform osmotic extraction, the obtained extract was centrifuged at 3,000 rpm for 10 minutes. The supernatant was subjected to evaporation to solidify the solvent by drying under reduced pressure. Then, the obtained solid was redissolved in 1.0 ml solvent (mobile phase A/mobile phase B=50/50) to be used as an HPLC specimen. D7000 series (Manufactured by Hitachi) was used for the HPLC analysis and Capcell Pack UGL 205 μm 4.6Φ×250 mm (manufactured by Shiseido) was used as the column. For the mobile phase, a solution comprising 0.05% phosphate buffer solution (containing EDTA) and ethyl acetate-methanol (1:10) mixed at 8:2 was used as the mobile phase A, and 2% ethyl acetate-containing methanol was used as the mobile phase B. The flow rate was 1.0 ml/minute by the gradient method. SPD-10AVP UV-VIS detector was used for detection, and the detection wavelengths were 254 nm and 280 nm.
Results of Measurement of Cell Count and Equol Production Ability of *Lactococcus garvieae*

The measurement results are shown in Table 1. The results reveal that if the pH of the mother starter and bulk starter was 5 or higher, even if the pH of the fermented product after the main fermentation and the fermented soybean food was 4.6 or lower, a fermented soybean food containing *Lactococcus garvieae* retaining equol production ability could be prepared. Note that the cell count per se of *Lactococcus garvieae* in the fermented soybean food was observed to stay constant for a long period of time, while being little affected by the pH or the presence or absence of the equol production ability.

TABLE 1

| | pH | *Lactococcus garvieae* cell count (CFU/ml) | Equol production ability *1 | Sensory evaluation |
|---|---|---|---|---|
| Mother starter | 6.64 | $7.1 \times 10^8$ | ○ | — |
| Bulk starter | 6.72 | $8.0 \times 10^8$ | ○ | — |
| Fermented product after main fermentation | 4.56 | $5.7 \times 10^8$ | ○ | — |
| Fermented soybean food Immediately after preparation | 4.58 | $1.2 \times 10^8$ | ○ | Satisfactory |
| 1 week after | 4.38 | $3.0 \times 10^7$ | ○ | Satisfactory |
| 2 weeks after | 4.37 | $1.1 \times 10^7$ | ○ | Satisfactory |
| 3 weeks after | 4.32 | $1.3 \times 10^7$ | ○ | Satisfactory |
| 4 weeks after | 4.24 | $3.0 \times 10^6$ | ○ | Satisfactory |

*1 Equol production ability was measured with n = 2, and the determination was Δ when only one instance of equol production ability was observed, and ○ when equol production ability was observed in both cases.

Taste Evaluation

The fermented soybean food immediately after preparation and the fermented soybean food after 3 weeks' storage were satisfactory as foods with good soybean flavor, and no foreign taste or foreign odor.

Comparative Example 1

Preparation of Fermented Soybean Food and Evaluation of the Fermented Soybean Food The preparation of the mother starter, preparation of the bulk starter and the main fermentation to prepare a fermented soybean food (Comparative Example 1-1) were performed in the same conditions as in Example 1, except that the amount of glucose added was modified from 0.1 wt % to 1.0 wt % in the preparation of the mother starter.

Furthermore, the preparation of the mother starter, preparation of the bulk starter and the main fermentation to prepare a fermented soybean food (Comparative Example 1-2) were performed in the same conditions as in Example 1, except that the amount of glucose added was modified from 0.1 wt % to 1.0 wt % in the preparation of the bulk starter.

The pH, the cell count of the *Lactococcus garvieae* 20-92 strain and the presence or absence of the equol production ability of the fermented soybean food of Comparative Examples 1-1 and 1-2 were evaluated as in Example 1. In addition, the cell count of the *Lactococcus garvieae* 20-92 strain, and the presence or absence of equol production ability were also measured in the same fashion for the mother starter, the bulk starter and the main fermentation solution.

The results are shown in Table 2. In Comparative Example 1-1, which used a medium in which the pH decreases in the mother starter preparation, although no difference was observed in the cell count of the *Lactococcus garvieae* 20-92 strain, the equol production ability was lost. Similarly in the subsequent bulk starter, main fermentation solution preparation and fermented soybean food preparation, although no large differences from Example 1 were observed in the cell count, pH and sensory aspects, the equol production ability did not improve. In addition, as with Comparative Example 1-1, which used a medium in which the pH decreases during the bulk starter preparation, although no difference in the cell count of the *Lactococcus garvieae* 20-92 strain was observed, the equol production ability was lost. Similarly in the subsequent main fermentation and fermented soybean food preparation, although no large differences were observed in the cell count, pH and sensory aspects, the equol production ability did not improve.

TABLE 2

| | | pH | *Lactococcus garvieae* cell count (CFU/ml) | Equol production ability *1 | Sensory evaluation |
|---|---|---|---|---|---|
| Comparative Example 1-1 | Mother starter | 4.51 | $6.8 \times 10^8$ | x | — |
| | Bulk starter | 6.73 | $7.2 \times 10^8$ | x | — |
| | Fermented product after main fermentation | 4.55 | $6.2 \times 10^8$ | x | — |
| | Fermented soybean food | 4.56 | $1.3 \times 10^8$ | x | Satisfactory |
| Comparative Example 1-2 | Mother starter | 6.72 | $8.2 \times 10^8$ | ○ | — |
| | Bulk starter | 4.52 | $7.9 \times 10^8$ | x | — |
| | Fermented product after main fermentation | 4.54 | $5.8 \times 10^8$ | x | — |
| | Fermented soybean food | 4.55 | $1.8 \times 10^8$ | x | Satisfactory |

*1 Equol production ability was measured with n = 2, and the determination was Δ when only one instance of equol production ability was observed, ○ when equol production ability was observed in both cases, and x when no equol production ability was observed.

Example 2

Preparation of Fermented Milk by the Second Method, and Evaluation of the Fermented Milk 1. Preparation of Fermented Milk

*Lactococcus garvieae* (*Lactococcus* 20-92 strain, FERM BP-10036) having equol production ability was used to carry out the preparation of the mother starter, the preparation of the bulk starter, the main fermentation, and the container filling under the following conditions.

Preparation of Mother Starter

A mother starter medium was prepared by autoclave sterilization (115° C., 15 minutes) of 500 mL of a solution (pH 6.14) containing 10 wt % of non-fat dry milk, 6.67 wt % of fresh cream, 0.1 wt % of yeast extract ("SK yeast extract Hi-K", Nippon Paper Chemicals Co., Ltd.), 0.025 wt % of soybean hypocotyl extract ("Soya Flavone HG", Fuji Oil Co., Ltd.; the content of the daidzein species in the soybean hypocotyl extract is approximately 37 wt %) and the remainder in purified water. This starter medium was inoculated with an inoculum of *Lactococcus* 20-92 strain, and an anaerobic culture was carried out with a gas pack at 37° C. for 24 hours to obtain a mother starter.

Preparation of Bulk Starter

A bulk starter medium was prepared by UHT (Ultra High Temperature) sterilization (140° C., 4 seconds) of 10 L of a solution containing 10 wt % of non-fat dry milk, 6.67 wt % of fresh cream, 0.1 wt % of yeast extract ("SK yeast extract Hi-K", Nippon Paper Chemicals Co., Ltd.), 0.025 wt % of soybean hypocotyl extract ("Soya Flavone HG", Fuji Oil Co., Ltd.) and the remainder in purified water. The bulk starter medium recovered after UHT sterilization was inoculated with the mother starter obtained above to an amount of 1 v/v %, and an aerobic culture was carried out at 37° C. for 24 hours to obtain a bulk starter.

Main Fermentation

The main fermentation medium was prepared by UHT (Ultra High Temperature) sterilization (140° C., 4 seconds) of 10 L of a solution containing 10 wt % of non-fat dry milk, 6.67 wt % of fresh cream, 0.1 wt % of yeast extract ("SK yeast extract Hi-K", Nippon Paper Chemicals Co., Ltd.), 0.025 wt % of soybean hypocotyl extract ("Soya Flavone HG", Fuji Oil Co., Ltd.) and the remainder in purified water. The main fermentation medium recovered after UHT sterilization was inoculated with the bulk starter obtained above to an amount of 1 v/v %, and an aerobic culture was carried out at 37° C. for 24 hours to obtain a fermented milk.

Container Filling

The fermented milk obtained by the above main fermentation was introduced in a sterilized 600 mL capacity container in a sterile manner, and a given amount of lactic acid was further introduced into the container in a sterile manner; after mixing, the container was sealed.

2. Evaluation of Equol Production Ability of *Lactococcus garvieae* Contained in Fermented Milk Each of the sealed fermented milks obtained above were stored at 10° C. for 74 weeks. The pH of the fermented milk was measured immediately after preparation, 2 weeks after preparation, weeks after preparation, and 74 weeks after preparation; furthermore, the cell count of *Lactococcus garvieae* contained in the fermented milk, and the presence or absence of the equol production ability of *Lactococcus garvieae* contained in the fermented milk were evaluated by methods as the same as those in Example 1. In addition, the cell count of *Lactococcus garvieae*, and the equol production ability of *Lactococcus garvieae* contained in the fermented milk were also measured for the mother starter and the bulk starter prepared above.

The results are shown in Table 3. These results reveal that when the pH of the fermented milk was 4.6 or higher, fermented milk containing *Lactococcus garvieae* retaining equol production ability could be prepared. In addition, the equol production ability of *Lactococcus garvieae* was observed to be stably retained for 2 weeks if the pH of the fermented milk was 5.28 or higher, 6 weeks if the pH of the fermented milk was 5.79 or higher, and 74 weeks if the pH of the fermented milk was 5.92 or higher. On the other hand, the equol production ability of *Lactococcus garvieae* was revealed to be lost when the pH of the fermented milk was 4.09 and 3.53, even immediately after preparation. Note that the cell count per se of *Lactococcus garvieae* in the fermented milk was observed to stay constant for a long period of time while being little affected by the pH, or the presence or absence of the equol production ability.

TABLE 3

| | | Amount of lactic acid added (amount of lactic acid added to the container/amount of fermented milk contained in the container) | pH | *Lactococcus garvieae* cell count (cfu/ml) | Equol production ability #1 |
|---|---|---|---|---|---|
| Mother starter | | — | 5.94 | $5.9 \times 10^8$ | ○ |
| Bulk starter | | — | 6.08 | $4.3 \times 10^8$ | ○ |
| Fermented milk | Immediately after preparation | 0 mL/500 g | 6.06 | $4.1 \times 10^8$ | ○ |
| | | 6 mL/467.1 g | 5.64 | $3.4 \times 10^8$ | ○ |
| | | 18.4 mL/459.4 g | 5.12 | $3.9 \times 10^8$ | ○ |
| | | 35.5 mL/474.0 g | 4.60 | $2.5 \times 10^8$ | ○ |
| | | 53.3 mL/463.4 g | 4.09 | $2.0 \times 10^8$ | x |
| | | 96.6 mL/449.1 g | 3.53 | $1.5 \times 10^8$ | x |
| | 2 weeks after | 0 mL/500 g | 6.10 | $4.9 \times 10^8$ | ○ |
| | | 6 mL/467.1 g | 5.85 | $3.6 \times 10^8$ | ○ |
| | | 18.4 mL/459.4 g | 5.28 | $3.4 \times 10^8$ | x |
| | | 35.5 mL/474.0 g | 4.63 | $6.1 \times 10^7$ | x |
| | 6 weeks after | 0 mL/500 g | 5.99 | $3.7 \times 10^8$ | ○ |
| | | 6 mL/467.1 g | 5.79 | $3.2 \times 10^8$ | ○ |
| | | 18.4 mL/459.4 g | 5.24 | $3.4 \times 10^8$ | x |
| | | 35.5 mL/474.0 g | 4.62 | $2.5 \times 10^6$ | x |
| | 74 weeks after | 0 mL/500 g | 5.92 | $2.3 \times 10^8$ | ○ |
| | | 6 mL/467.1 g | 5.72 | $1.2 \times 10^8$ | x |

1 Equol production ability was measured with n = 3, and the determination was x when equol production ability was not observed in all of the three cases, and ○ when equol production ability was observed in all three cases.

Taste Evaluation

The fermentation milk (no lactic acid addition) immediately after preparation and the fermentation milk (no lactic acid addition) after 74 weeks of storage were both satisfactory as foods with no sourness and, moreover, easy drinkability.

Example 3

Preparation of Fermented Milk by the Second Method, and Evaluation of the Fermented Milk The preparation of the mother starter, preparation of the bulk starter and the main fermentation were carried out in the same conditions as in the above Example 2, except that as the mother starter medium, bulk starter medium and the main fermentation medium, those prepared by adding given amounts of the fermentation-promoting agents shown in Table 4 to a medium based on the composition described below were used.

<Medium Composition>

| | |
|---|---|
| Non-fat dry milk | 10 wt % |
| Fresh cream | 6.67 wt % |
| Soybean hypocotyl extract | 0.025 wt % |
| ("Soya Flavone HG", Fuji Oil Co., Ltd.) | |
| Fermentation-promoting agent shown in Table 2 | Concentration shown in Table 2 |
| Purified water | remainder |
| Total | 100 wt % |

TABLE 4

| | Mother starter medium | Bulk starter medium | Main fermentation medium |
|---|---|---|---|
| Condition A-1 | 0.1 wt % yeast extract | 0.1 wt % yeast extract | 0.1 wt % yeast extract |
| Condition A-2 | 0.1 wt % yeast extract | 0.1 wt % yeast extract | 0.05 wt % yeast extract |
| Condition A-3 | 0.1 wt % yeast extract | 0.1 wt % yeast extract | 0.025 wt % yeast extract |
| Condition A-4 | 0.1 wt % yeast extract | 0.1 wt % yeast extract | 0.0125 wt % yeast extract |
| Condition B | 0.1 wt % whey hydrolysate | 0.1 wt % whey hydrolysate | 0.1 wt % whey hydrolysate |
| Condition C | 0.1 wt % casein/yeast hydrolysate | 0.1 wt % casein/yeast hydrolysate | 0.1 wt % casein/yeast hydrolysate |

Product name "SK yeast extract Hi-K" (manufactured by Nippon Paper Chemicals Co., Ltd.) was used for the yeast extract.
"FE135" (manufactured by DMV Japan) was used for the whey hydrolysate.
"FE150" and "FE135" (manufactured by DMV Japan) were used for the casein/yeast hydrolysate.

500 g of fermented milk obtained in this manner was introduced into a sterilized 600 mL capacity container in a sterile manner, and stored at 10° C. for 10 weeks.

Immediately after preparation, 2 weeks after preparation, 4 weeks after preparation, and 10 weeks after preparation, the pH of the fermented milk was measured; furthermore, the cell count of Lactococcus garvieae contained in the fermented milk, and the presence or absence of the equol production ability of Lactococcus garvieae contained in the fermented milk were evaluated by methods as the same as those in Example 1. In addition, for the mother starter and the bulk starter, the cell count of Lactococcus garvieae, and the equol production ability of Lactococcus garvieae contained in fermented milk were also measured in same fashion.

The obtained results are shown in Table 5. These results reveal that the equol production ability of Lactococcus garvieae could be retained by adding yeast extract, whey hydrolysate or casein/yeast hydrolysate to the medium. In particular, it was found that if the medium contained 0.1 wt % or more yeast extract or 0.1 wt % or more casein/yeast hydrolysate, the equol production ability of Lactococcus garvieae in the fermented milk could be stably retained over a period as long as 10 weeks or more.

TABLE 5

| | | Storage condition | pH | Lactococcus garvieae cell count (cfu/ml) | Equol production ability #1 |
|---|---|---|---|---|---|
| Mother starter | | Condition A-1 to A-5 | 5.64 | $7.0 \times 10^8$ | o |
| | | Condition B | 5.65 | $5.2 \times 10^8$ | o |
| | | Condition C | 5.66 | $5.8 \times 10^8$ | o |
| Bulk starter | | Condition A-1 to A-5 | 6.02 | $6.1 \times 10^8$ | o |
| | | Condition B | 5.95 | $7.0 \times 10^8$ | o |
| | | Condition C | 6.05 | $5.3 \times 10^8$ | o |
| Fermented milk | Immediately after preparation | Condition A-1 | 6.00 | $5.9 \times 10^8$ | o |
| | | Condition A-2 | 6.03 | $5.8 \times 10^8$ | o |
| | | Condition A-3 | 6.11 | $4.0 \times 10^8$ | o |
| | | Condition A-4 | 6.20 | $2.3 \times 10^8$ | o |
| | | Condition B | 5.93 | $5.7 \times 10^8$ | o |
| | | Condition C | 6.02 | $4.6 \times 10^8$ | o |
| | 2 weeks after | Condition A-1 | 6.04 | $3.9 \times 10^8$ | o |
| | | Condition A-2 | 6.07 | $3.9 \times 10^8$ | o |
| | | Condition A-3 | 6.16 | $2.8 \times 10^8$ | o |
| | | Condition A-4 | 6.24 | $2.2 \times 10^8$ | o |
| | | Condition B | 5.99 | $5.0 \times 10^8$ | o |
| | | Condition C | 6.08 | $4.7 \times 10^8$ | o |
| | 4 weeks after | Condition A-1 | 5.99 | $3.0 \times 10^8$ | o |
| | | Condition A-2 | 6.04 | $3.0 \times 10^8$ | o |
| | | Condition A-3 | 6.12 | $2.6 \times 10^8$ | x |
| | | Condition A-4 | 6.23 | $2.1 \times 10^8$ | x |
| | | Condition B | 5.95 | $5.1 \times 10^8$ | o |
| | | Condition C | 6.03 | $4.8 \times 10^8$ | o |
| | 10 weeks after | Condition A-1 | 5.89 | $2.8 \times 10^8$ | o |
| | | Condition A-2 | 6.03 | $2.2 \times 10^8$ | x |
| | | Condition A-3 | 6.10 | $1.9 \times 10^8$ | x |
| | | Condition A-4 | 6.20 | $1.3 \times 10^8$ | x |
| | | Condition B | 5.89 | $3.4 \times 10^8$ | x |
| | | Condition C | 5.98 | $4.4 \times 10^8$ | o |

1 Equol production ability was measured with n = 3, and the determination was x when equol production ability was not observed, and o when equol production ability was observed in all three cases.

Comparative Example 2

Preparation of Fermented Milk and Evaluation of the Fermented Milk

The preparation of the mother starter, preparation of the bulk starter and the main fermentation were carried out in the same condition as in Example 2, except that aerobic culture was performed in the preparation of the mother starter.

The pH of the fermented milk obtained in this manner was measured; furthermore, the cell count of Lactococcus garvieae contained in the fermented milk, and the presence or absence of the equol production ability of Lactococcus garvieae contained in the fermented milk were evaluated by methods as the same as those in Example 2. In addition, for the mother starter and the bulk starter, the cell count of Lactococcus garvieae, and the equol production ability of Lactococcus garvieae contained in fermented milk were also measured in same fashion.

As a result, when the mother starter was prepared by aerobic fermentation in aerobic conditions, although the equol production ability of *Lactococcus garvieae* in the mother starter was maintained, the equol production ability of *Lactococcus garvieae* in the fermented milk product obtained was ultimately lost. Note that, even if the mother starter was prepared by aerobic fermentation, the pH and the, cell count of *Lactococcus garvieae* in the fermented milk were on the same order as when the mother starter was prepared by anaerobic fermentation.

Example 4

Evaluation of the Retention Effect of the Equol Production Ability of the Equol-Producing Microorganism 1. Preparation of Equol-Producing Microorganism-Containing Composition An inoculum of *Lactococcus garvieae* (*Lactococcus* 20-92 strain, FERM BP-10036) was inoculated into 5 mL of modified GAM medium (manufactured by Nissui Pharmaceutical Co., Ltd.), and an anaerobic culture was carried out with a gas pack at 37° C. for 24 hours. Then, 50 mL of modified GAM medium (Nissui Pharmaceutical Co., Ltd.) was inoculated with 2 mL of the obtained culture, and anaerobic culture was carried out with a gas pack at 37° C. for 24 hours. Further, 200 mL of modified GAM medium (Nissui Pharmaceutical Co., Ltd.) was inoculated with 8 mL of the obtained culture, and anaerobic culture was carried out with a gas pack at 37° C. for 24 hours.

The obtained culture was centrifuged (4,500 rpm×15 minutes) to recover the cell bodies, and the obtained cells were added to each beverage of the compositions shown in Table 6 so that the cell concentration was about $1 \times 10^8$ cfu/mL to prepare an equol-producing microorganism-containing composition; the composition was then divided into 15 mL-capacity polypropylene tubes (made by IWAKI) in 10 mL aliquots.

TABLE 6

| | Composition |
|---|---|
| Beverage 1 | Beverage adjusted to pH 4.5 by adding (citric acid) to a soybean powder solution (containing 14% soybean powder by dry weight) |
| Beverage 2 | Beverage in which ascorbic acid was added to a soybean powder solution (containing 14% soybean powder by dry weight) to an amount of 0.5 wt %, adjusted to pH 4.5 using (citric acid) |
| Beverage 3 | Beverage in which ascorbic acid was added to a soybean powder solution (containing 14% soybean powder by dry weight) to an amount of 1.0 wt %, adjusted to pH 4.5 using (citric acid) |
| Beverage 4 | Beverage in which ascorbic acid was added to a soybean powder solution (containing 14% soybean powder by dry weight) to an amount of 2.0 wt %, adjusted to pH 4.5 using (citric acid) |

1. Evaluation of Equol Production Ability After Storage

Each of the equol-producing microorganism-containing compositions obtained above was stored at 10° C. for 21 days. During the storage period, evaluations of pH, cell count and equol production ability, were performed for each equol-producing microorganism-containing composition. The method for measuring the cell count was the same as in the above Example 1. In addition, the equol production ability was analyzed by HPLC in the same manner as in the above Example 1 was performed, and the equol conversion rate was calculated according to the following formula.

$$\text{Equol conversion rate (\%)} = \{(\text{equol peak area})/(\text{total peak area of daidzein, dihydrodaidzein and equol})\} \times 100 \quad [\text{Math. 1}]$$

Figure 1:
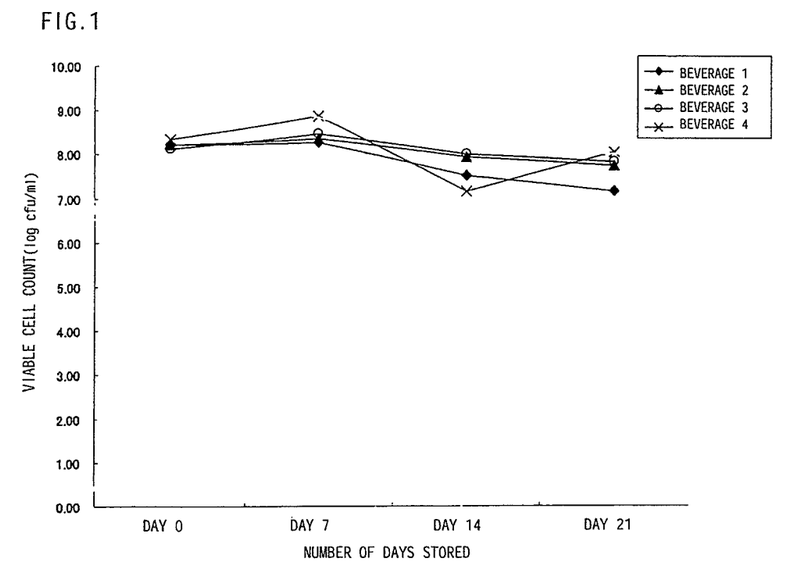
FIG. 1 shows the results of measurements of the viable cell count of the *Lactococcus* strain contained in each beverage in Example 4.
Figure 2:
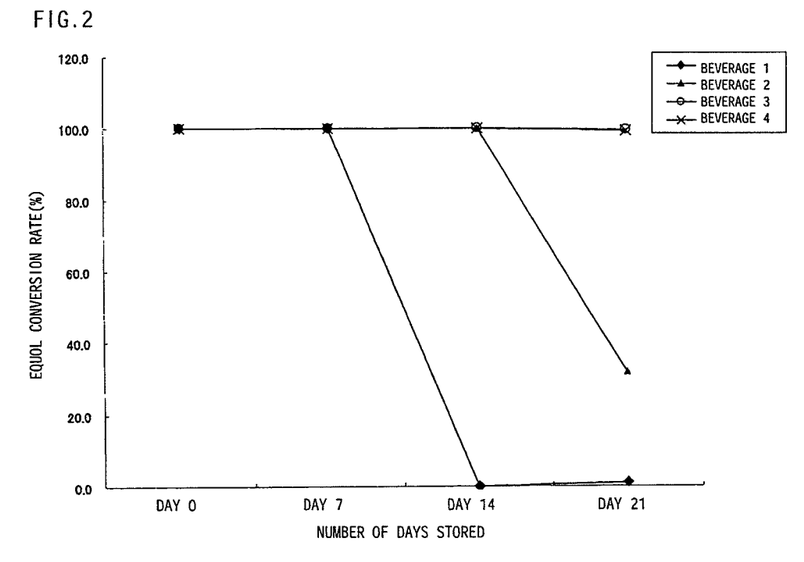
FIG. 2 shows the results of measurements of the equol production ability of the *Lactococcus* strain contained in each beverage in Example 4.

The results of the pH measurement are shown in Table 7. In addition, the results of the cell count measurement are shown in FIG. 1, and the results of the equol production ability measurement are shown in FIG. 2. As is clear from Table 7, in all of the beverages, the pH immediately after preparation was maintained even when stored, and an environment in which contaminating bacteria could not proliferate was maintained inside the beverages. In addition, as is clear from FIG. 1, with each equol-producing microorganism-containing composition, little difference was observed in the viable cell count during the storage period. On the other hand, as shown in FIG. 2, although the equol production ability was lost 14 days after storage in the equol-producing microorganism-containing composition with no ascorbic acid added, in the equol-producing microorganism-containing compositions in which ascorbic acid was added, the equol production ability was maintained even after 21 days of storage. In particular, in the equol-producing microorganism-containing compositions with 1 wt % or 2 wt % ascorbic acid, the equol production ability was found to be maintained in extremely stable fashion.

TABLE 7 pH after storage of each beverage

| | Number of days after storage | | | |
|---|---|---|---|---|
| | 0 days later | 7 days later | 14 days later | 21 days later |
| Beverage 1 | 4.52 | 4.53 | 4.52 | 4.53 |
| Beverage 2 | 4.48 | 4.50 | 4.49 | 4.50 |
| Beverage 3 | 4.47 | 4.50 | 4.48 | 4.52 |
| Beverage 4 | 4.46 | 4.47 | 4.46 | 4.48 |

Example 5

Evaluation of the Retention Effect of the Equol Production Ability of the Equol-Producing Microorganism 1. Preparation of Equol-Producing Microorganism-Containing Composition A mother starter was obtained by inoculating 5 ml of a medium having the same composition as the mother starter medium used in Example 1 with an inoculum of *Lactococcus* 20-92 strain, and conducting an anaerobic culture with a gas pack at 37° C. for 96 hours.

Next, 10 ml of a medium having the same composition as the bulk starter medium used in Example 1 was inoculated with 0.2 ml of the mother starter obtained above, and an anaerobic culture was carried out for 15 hours using a gas pack at 37° C. to obtain a primary bulk starter. In addition, 300 ml of a medium having the same composition as the bulk starter medium used in Example 1 was inoculated with 6 ml of the mother starter obtained above, and an anaerobic culture was carried out for 15 hours using a gas pack at 37° C. to obtain a secondary bulk starter.

Next, 2,000 ml of a medium having the same composition as the main fermentation medium used in Example 1 was inoculated with 40 mL of the secondary bulk starter obtained above, and a stationary culture was carried out at 37° C. for 15 hours under aerobic conditions to obtain a fermented soybean solution.

Six types of antioxidants were added to the obtained fermented soybean solution, as shown in Table 8, to prepare a fermented product; afterward, paper cups were separately filled with 130 g of solution, and sealed with aluminum lids. These cups were stored at 10° C., opened 7 days later to measure the cell count of the equol-producing microorganisms, and the equol production ability thereof was measured by methods as the same as those in Example 4.

TABLE 8

| | Antioxidant | Concentration added in the fermented product | Product name of the antioxidant, and manufacturer |
|---|---|---|---|
| Example 5 | Ascorbic acid | 0.5 wt % | L-ascorbic acid (SIGMA) |
| Comparative Example 5-1 | Bayberry extract | 0.1 wt % | SANMELIN Y-AF (SAN-EI GEN F.F.I., Inc.) |
| Comparative Example 5-2 | Rutin | 0.1 wt % | SANMELIN A0-1007 (SAN-EI GEN F.F.I., Inc.) |
| Comparative Example 5-3 | Rosemary extract | 0.05 wt % | RM-21A base (MITSUBISHI-KAGAKU FOODS CORPORATION) |
| Comparative Example 5-4 | Tea extract | 0.03 wt % | Sunfood 100 (MITSUBISHI-KAGAKU FOODS CORPORATION) |
| Comparative Example 5-5 | Vitamin E | 0.25 wt % | VE liquid extract (MITSUBISHI-KAGAKU FOODS CORPORATION) |

2. Evaluation Result

The result from the measurement of cell count of equol producing microorganism is shown in Table 9, and the result from the measurement of equol production ability is shown in Table 10. At the start of storage, equol production ability was observed in all of the cases in which the oxidation inhibitor was mixed. However, 7 days after storage, aside from the fermented product to which ascorbic acid was added, the equol production capabilities disappeared in all of the cases.

TABLE 9

| | Equol-producing microorganism cell count (CFU/mL) | |
|---|---|---|
| | At 0 days storage | At 7 days storage |
| Example 5 | $3.8 \times 10^8$ | $1.4 \times 10^8$ |
| Comparative Example 5-1 | $3.6 \times 10^8$ | $2.0 \times 10^8$ |
| Comparative Example 5-2 | $3.2 \times 10^8$ | $1.7 \times 10^8$ |
| Comparative Example 5-3 | $4.0 \times 10^8$ | $2.8 \times 10^8$ |
| Comparative Example 5-4 | $3.2 \times 10^8$ | $1.8 \times 10^8$ |
| Comparative Example 5-5 | $4.0 \times 10^8$ | $3.6 \times 10^8$ |

TABLE 10

| | Equol conversion rate (%) | |
|---|---|---|
| | At 0 days storage | At 7 days storage |
| Example 5 | 98.5 | 100.0 |
| Comparative Example 5-1 | 98.8 | 0.0 |

TABLE 10-continued

| | Equol conversion rate (%) | |
|---|---|---|
| | At 0 days storage | At 7 days storage |
| Comparative Example 5-2 | 98.6 | 0.0 |
| Comparative Example 5-3 | 98.2 | 0.0 |
| Comparative Example 5-4 | 97.8 | 0.0 |
| Comparative Example 5-5 | 98.9 | 0.0 |

The invention claimed is:

1. A method for maintaining the equol production ability of an equol-producing microorganism in a fermented product, the method comprising:
    adding at least one member selected from the group consisting of ascorbic acid, derivatives thereof, and salts thereof to a composition containing an equol-producing microorganism in need of such maintaining, in the state of a living cell,
    wherein the at least one member is added to the composition at a proportion of 0.1 to 5 wt %.

2. The method according to claim 1, wherein the pH of the composition is 5.0 or lower.

3. The method according to claim 1, wherein the microorganism is contained at a concentration of $1 \times 10^5$ to $10^{10}$ cfu/g in the state of living cell.

4. The method according to claim 1, wherein the composition is a fermented food.

5. The method according to claim 4, wherein the fermented food is a fermented soybean beverage or a fermented soybean milk.

6. The method according to claim 4, which fermented food is stored at 10° C. or lower.

7. The method according to claim 1, wherein the equol-producing microorganism is a lactic acid bacterium.

8. The method according to claim 7, wherein the equol-producing microorganism is *Lactococcus garvieae*.

9. A method for producing a fermented product containing an equol-producing microorganism, the method comprising:
    preparing a composition containing an equol-producing microorganism, in the state of a living cell; and adding to the composition an effective amount of at least one member selected from the group consisting of ascorbic acid, derivatives thereof, and salts thereof for maintaining the equol-producing ability of the microorganism in the fermented product
    wherein the at least one member is added to the composition at a proportion of 0.1 to 5 wt %.

10. The method according to claim 9, wherein the pH of the composition is 5.0 or lower.

11. The method according to claim 9, wherein the composition is a fermented food.

12. The method according to claim 11, wherein the fermented food is a fermented soybean beverage or a fermented soybean milk.

13. The method according to claim 11, which fermented food is stored at 10° C. or lower.

* * * * *